(12) United States Patent
Casagrande et al.

(10) Patent No.: US 6,872,684 B2
(45) Date of Patent: Mar. 29, 2005

(54) CATALYSTS FOR OXYCHLORINATION OF ETHYLENE TO 1,2-DICHLOROETHANE

(75) Inventors: Francesco Casagrande, Novara (IT); Carlo Orsenigo, Milan (IT)

(73) Assignee: Sud Chemie MT S.R.I., Milan (IT)

( * ) Notice: Subject to any disclaimer, the term of this patent is extended or adjusted under 35 U.S.C. 154(b) by 0 days.

(21) Appl. No.: 10/791,952

(22) Filed: Mar. 3, 2004

(65) Prior Publication Data

US 2004/0192978 A1 Sep. 30, 2004

(30) Foreign Application Priority Data

Mar. 31, 2003 (IT) ..................... MI2003A0630

(51) Int. Cl.[7] .................. B01J 27/122; B01J 27/138; B01J 23/02; C07C 17/15; C07C 17/152
(52) U.S. Cl. ............... 502/225; 502/226; 502/231; 502/340; 502/341; 502/345; 502/346; 570/224; 570/243; 570/245
(58) Field of Search ................ 502/225, 226, 502/231, 340, 341, 345, 346; 570/224, 243, 245

(56) References Cited

U.S. PATENT DOCUMENTS

| 4,115,323 | A | * | 9/1978 | Lemanski et al. | .......... 502/245 |
|---|---|---|---|---|---|
| 4,587,230 | A | * | 5/1986 | Cavaterra et al. | ............ 502/225 |
| 4,871,707 | A | * | 10/1989 | Cavaterra et al. | ............ 502/225 |
| 5,070,062 | A | * | 12/1991 | Canavesi et al. | ............ 502/225 |
| 5,334,789 | A | * | 8/1994 | Komatsu et al. | ............. 570/203 |
| 6,362,384 | B2 | * | 3/2002 | Meissner et al. | ........... 570/203 |
| 6,452,059 | B1 | * | 9/2002 | Casagrande et al. | ........ 570/245 |
| 6,759,365 | B2 | * | 7/2004 | Cavalli et al. | .............. 502/346 |
| 2001/0011149 | A1 | * | 8/2001 | MeiBner et al. | ............ 570/243 |

FOREIGN PATENT DOCUMENTS

| EP | 0494557 | 11/1991 |
|---|---|---|
| EP | 1306130 | 5/2003 |
| GB | 1345653 | 1/1974 |
| WO | WO 99/34918 | 7/1999 |

* cited by examiner

Primary Examiner—Mark L. Bell
Assistant Examiner—Patricia L. Hailey
(74) Attorney, Agent, or Firm—Welsh & Katz, Ltd.

(57) ABSTRACT

Catalysts for oxychlorination of ethylene to 1,2-dichloroethane, comprising compounds of copper and magnesium supported on alumina, in which the copper, expressed as metal, is present in an amount of 7 to 12% by weight and the Mg/Cu ratio is 0.05 to 1, and wherein the ratio between the concentration of copper provided by the Al/Cu ratio at the surface and that provided by the Al/Cu ratio in the entire particle of the catalyst is from 0.8 to 1.3.

9 Claims, No Drawings

CATALYSTS FOR OXYCHLORINATION OF ETHYLENE TO 1,2-DICHLOROETHANE

The present invention relates to a catalyst for oxychlorination of ethylene to 1,2-dichloroethane (1,2-DCE), to a method for preparing it and to its use in the oxychlorination process.

BACKGROUND OF THE INVENTION

Catalysts for oxychlorination of ethylene to 1,2-DCE that comprise a copper compound, generally cupric chloride, and promoters based on salts of alkali and/or alkaline-earth metals and rare earth metals are well-known in the literature.

The copper content of these catalysts is generally not higher than 6–8% by weight.

Catalysts with a copper content that can reach 12–14% by weight are also known. Examples of these catalysts are disclosed in patent GB 1,189,815.

The catalysts are prepared by coprecipitation of hydrogels of alumina and copper, followed by aging of the precipitate at 10 to 40° C. for at least 10 hours, drying and washing and finally calcining at temperatures between 300 and 600° C. for a time sufficient to convert the alumina hydrogel into gamma alumina.

The catalysts are preferably used in a fluidized bed.

Differently from catalysts that have a high copper content (12% by weight) obtained by impregnation of alumina with a solution of a copper salt, which according to the patent cited above provide low conversions of hydrochloric acid and considerable combustion of the ethylene to CO and $CO_2$, catalysts prepared by coprecipitation allow to obtain, in the operating conditions cited in the patent, a good performance in terms of conversion and selectivity and in terms of stability of the fluidized bed.

However, the drawback of these catalysts is due to the fact that it is necessary to work with high spatial velocities, i.e., with short contact times and accordingly with a considerable recycling of the unconverted ethylene.

Commercial catalysts with a high copper content (12–13% by weight) are known which are probably prepared by means of the coprecipitation method and which cause a considerable combustion of the ethylene even when operating at relatively low temperatures (210° C.).

SUMMARY OF THE INVENTION

It has now been found unexpectedly that it is possible to obtain catalysts for oxychlorination of ethylene to 1,2-DCE with high copper content, prepared by impregnating alumina, that do not suffer the drawbacks of the catalysts of the known art obtained by coprecipitation, but instead provide good performance both in terms of molar selectivity to 1,2-DCE and in terms of productivity (kg of 1,2-DCE/kg of catalyst per hour).

DETAILED DESCRIPTION OF THE INVENTION

The copper content of the catalysts according to the invention varies from 7 to 12% by weight; such catalysts comprise, in addition to the copper compounds, magnesium compounds in such a quantity that the Mg/Cu ratio is comprised between 0.05 and 1.

The distribution of copper in these catalysts is such that the X/Y ratio, where X is the Al/Cu ratio determined by XPS (X-ray Photoemission Spectroscopy) and Y is the Al/Cu ratio in the entire particle, is in the range of 0.8 to 1.3.

Copper and magnesium compounds preferably used are the chlorides.

The catalysts can also comprise, in addition to a copper and magnesium compound, promoters chosen among compounds of alkali metals, alkaline-earth metals and rare earth metals or mixtures thereof. Chlorides of potassium, rubidium and cesium, and mixtures thereof, are preferred.

The alumina has a surface area comprised from 90 and 260 $m^2/g$ and a pore volume of 0.4–0.6 $cm^3/g$. The surface area of the catalysts varies from 60 to 150 $m^2/g$. Preferably, gamma alumina is used with pore volume from 0.15 to 0.35 $cm^3/g$.

Preferably, the particle size distribution of the alumina consists of at least 60% of particles with size between 60 and 125 microns.

The catalyst is prepared by impregnating the alumina in two or more steps, in which the volume of solution of the copper salt and magnesium that is used is equal to, preferably lower than, the volume of the pores of the alumina during the first impregnation, is lower than the volume used for first impregnation, for example 60% of pore volume, during the second impregnation, and is even lower, for example 40% of pore volume, during the third impregnation.

The triple impregnation is preferably used when the copper content of the compound to be supported is higher than 9–10% by weight.

The powder of the first impregnation is dried at 100–130° C. for a sufficient time, for example 16 hours, in a stove; this is followed by the second impregnation and by drying the resulting powder in a stove, and so forth for the subsequent impregnations.

The solution of salts is prepared by dissolving said salts in distilled water, facilitating dissolution by mild heating: the solution is then sprayed onto the alumina arranged in a rotating container. It is also possible to work in a fluidized bed.

The solutions are preferably acid for hydrochloric acid or other strong acids used in quantities from 0.1 to 1 equivalent per gram atom of copper. These solutions are used in particular when the copper to be fixed is more than 9–10%.

Copper distribution is determined by the XPS method, used to measure the concentration of copper atoms (i.e., the Al/Cu ratio) in a surface layer of 2–3 nm.

For further indications on the XPS method, reference is made to U.S. Pat. Nos. 4,587,230 and 4,871,707.

The oxychlorination process is preferably performed in a fluidized bed according to known methods, working at temperatures between 190 and 235° C. and using temperatures that rise as the magnesium content of the catalyst rises.

The high active copper content of the catalyst ensures good performance in terms of DCE yield and in terms of productivity even when working at the relatively low temperatures cited above.

The process is performed preferably with Cl/C reaction ratios of 0.60–0.7, $O_2$/ethylene molar reaction ratios of 0.4–0.5, and with a linear velocity of 20–22 cm/s and contact times of 5–6 seconds.

The following examples are provided to illustrate but not to limit the scope of the present invention.

EXAMPLE 1

1600 g of gamma alumina were spray-impregnated a first time in a 5-liter rotating jar at ambient temperature with 720 ml of an aqueous solution having a total volume of 1200 ml and containing:
$CuCl_2 2H_2O$: 481.5 g
$MgCl_2 6H_2O$: 187.7 g
remainder: demineralized water to a volume of 1200 ml.

The volume of 720 ml was added gradually in the jar.

The impregnated powder was dried at 110° C. for 16 hours in a stove previously brought to the chosen temperature.

This was followed by a second impregnation with the remaining volume of solution (480 ml) and by final drying at 110° C. for 16 hours.

The alumina used had the following characteristics:
surface area: 218 $m^2/g$;
pore volume: 0.50 $cm^3/g$;
particle size distribution with particles having a diameter:
higher than 125 microns=4.8%
90 to 125 microns=35.2%
63 to 90 microns=44.4%
40 to 63 microns=13.9%
lower than 40 microns=1.7%

The catalyst had a surface area of 119 $m^2/g$, a pore volume of 0.22 $cm^3/g$, an average pore radius of 3.7 nm, an apparent density of 1.77 $g/cm^3$, and a bulk density of 1.16 $g/cm^3$; 78% of the particles had a size between 63 and 125 microns, 8% between 40 and 63 microns, 2.2% higher than 125 microns, and 1.9% lower than 40 microns.

The Cu content by weight was 7.82%; the Mg content was 1.02%.

The bulk Al/Cu ratio (Y) was 12.7 and the XPS Al/Cu ratio (2–3 nm layer) was 11.6; the X/Y ratio was 0.91.

The catalyst was tested in a glass reactor provided with a system for controlling the supply and dosage of the reagents and with a cooling system for condensing and recovering the condensable products.

The incondensable fractions were measured by gas chromatography.

During the test, the condensed products were collected in two phases, an aqueous one and an organic one. The two phases were separated and weighed; the hydrochloric acid was analyzed by gas chromatography in order to determine DCE purity and check the quantity of chlorinated byproducts.

The dimensions of the reactor were: inside diameter, 20.6 mm; height, 3200 mm.

The tests were conducted at the pressure of 1.6 atmospheres, with a linear velocity of 21–22 cm/s, working at temperatures between 210 and 230 ° C. Oxygen was used as oxidizer, the Cl/C ratio was 0.60–0.65, and the $O_2/C_2H_4$ ratio was 0.41–0.44.

The productivity of the catalyst is expressed in kg of pure DCE per liter of catalyst per hour.

The results achieved are listed in the table.

EXAMPLE 2

1500 g of gamma alumina having the characteristics of Example 1 were impregnated a first time in a 5-liter rotating jar at ambient temperature with 675 ml of an aqueous solution having a total volume of 1500 ml that contained:
$CuCl_2 2H_2O$=777.9 g
$MgCl_2 6H_2O$=303.9 g
HCl 37% by weight=65.0 ml
remainder: demineralized water to a volume of 1500 ml.

The powder was dried at 110° C. for 16 hours in a stove previously brought to the chosen temperature. This was followed by a second impregnation with 450 ml of the remaining volume of solution and by subsequent drying at 110° C. in a stove.

This was followed by a third impregnation with 375 ml of the remaining volume of solution and drying at 110° C. for 16 hours in a stove.

The catalyst contained 11.49% by weight of Cu and 1.47% by weight of Mg; the Y ratio was 7.6 and the X ratio was 9; X/Y was 1.18. Surface area was 90.6 $m^2/g$, pore volume 0.19 $cm^3/g$, average radius 4.2 nm, apparent density 1.89 $g/cm^3$, and bulk density 1.21 $g/cm^3$.

Particle size distribution comprised particles with the following diameters (in microns): 77% has a diameter between 63 and 125 microns; 15.8% had a diameter between 40 and 63 microns; 6.2% had a diameter of less than 40 microns.

The catalyst was used in oxychlorination tests in the conditions of Example 1.

The productivity of the catalyst is expressed in kg of pure DCE per liter of catalyst and per hour.

The results are given in the table.

COMPARISON EXAMPLE 1

1200 g of alumina having the characteristics of Example 1 were impregnated in a 5-liter rotating jar with 540 ml of a solution that contained:
$CuCl_2 2H_2O$=282.1 g
$MgCl_2 6H_2O$=135.3 g
HCl 37% by weight=48.0 ml The powder was then dried in the conditions of Example 1.

The catalyst contained 6.31% by weight of Cu and 1.00% by weight of Mg. The X/Y ratio was 1.8, the surface area 93 $m^2/g$, the pore volume 0.26 $cm^3/g$, and the average radius 5.6 nm. The particle size distribution was similar to Example 1.

The catalyst was used in oxychlorination tests in the conditions of Example 1.

The results are reported in the table.

The productivity of the catalyst of this example, as well as of Comparison Example 2, is expressed in kg of pure DCE per liter of catalyst per hour.

COMPARISON EXAMPLE 2

A commercial catalyst supported on gamma alumina, containing 12.50% by weight of copper and 5.58% by weight of chlorine, and in which the X/Y ratio was 3, the surface area 237 $m^2/g$, the pore volume 0.34 $cm^3/g$, the average pore radius 2.9 nm, the apparent density 1.56 $g/cm^3$, 58% of the particles had dimensions between 63 and 125 microns, 20.5% measured between 40 and 63 microns and 15.9% less than 40 microns, was tested in the conditions of Example 1. The results are given in the table.

The disclosures in Italian Patent Application No. MI2003A000630 from which this application claims priority are incorporated herein by reference.

TABLE

| Catalyst | HCl conv. % | molar % selectivity of $C_2H_4$ to | | | Molar % of DCE purity | Productivity kg DCE/l cat hour |
| --- | --- | --- | --- | --- | --- | --- |
| | | DCE | COx | Various chlorides | | |
| AVERAGE REACTION TEMPERATURE = 210° C. | | | | | | |
| Ex. 1 | 99.92 | 98.01 | 1.60 | 0.39 | 99.60 | 0.51 |
| Comp. Ex. 1 | 99.91 | 97.87 | 1.77 | 0.53 | 99.63 | 0.50 |
| Comp. Ex. 2 | 99.93 | 94.61 | 5.00 | 0.39 | 99.60 | 0.50 |

TABLE-continued

| Catalyst | HCl conv. % | molar % selectivity of $C_2H_4$ to | | | Molar % of DCE purity | Productivity kg DCE/l cat hour |
|---|---|---|---|---|---|---|
| | | DCE | COx | Various chlorides | | |
| AVERAGE REACTION TEMPERATURE = 220° C. | | | | | | |
| Ex. 1 | 99.94 | 97.26 | 2.35 | 0.39 | 99.59 | 0.50 |
| Ex. 2 | 99.96 | 97.76 | 1.82 | 0.42 | 99.57 | 0.51 |
| Comp. Ex. 1 | 99.92 | 96.98 | 2.58 | 0.44 | 99.55 | 0.50 |
| AVERAGE REACTION TEMPERATURE = 230° C. | | | | | | |
| Ex. 1 | 99.92 | 96.00 | 3.53 | 0.47 | 99.52 | 0.50 |
| Ex. 2 | 99.95 | 96.83 | 2.70 | 0.43 | 99.52 | 0.51 |
| Comp. Ex. 1 | 99.92 | 95.67 | 3.89 | 0.44 | 99.54 | 0.50 |

What is claimed is:

1. Catalysts for oxychlorination of ethylene to 1,2-dichloroethane, comprising compounds of copper and magnesium supported on alumina, in which copper, expressed as metal, is present in an amount of 7 to 12% by weight and the Mg/Cu ratio is from 0.05 to 1, wherein the distribution of copper in the particle of the catalyst is such that the X/Y ratio between the concentration of the copper atoms at the surface provided by the Al/Cu ratio (X) at the surface (layer of 20–30A) and the concentration given by the Al/Cu ratio (Y) in the entire particle is from 0.8 to 1.3.

2. the catalysts according to claim 1, wherein the copper compound is cupric chloride and the magnesium compound is magnesium chloride.

3. The catalysts according to claim 1, wherein the copper content is 9–12% by weight and the Mg/Cu ratio is 0.1–0.5.

4. The catalysts according to claim 1, having a surface area of 60 to 150 $m^2/g$.

5. The catalysts according to claim 1, comprising alkali metal compounds as promoters.

6. The catalysts according to claim 1 supported on gamma alumina.

7. A method for preparing the catalysts according to claim 1, comprising impregnating the alumina in two or more steps, wherein the first step uses volumes of aqueous solution of the Cu and Mg compounds that are equal to, or lower than, the volume of the pores of the alumina, and the subsequent steps use volumes that gradually decrease with respect to the volume used in the first step.

8. The method according to claim 7, wherein the alumina, after an impregnation step, is dried before an additional impregnation step.

9. A process for the oxychlorination of ethylene to 1,2-dichloroethane, conducted in a fluidized bed comprising the steps of contacting a catalyst as defined in any one of claims 1–6, ethylene and oxygen as an oxidizing agent, wherein the molar ratio of oxygen/ethylene is 0.4–0.5, the molar ratio of Cl/C is 0.6–0.7 and the oxychlorination temperature is comprised from 190° to 235° C.

* * * * *